United States Patent [19]

Chu

[11] Patent Number: 4,891,463

[45] Date of Patent: Jan. 2, 1990

[54] AROMATIZATION OF ALIPHATICS OVER A ZEOLITE CONTAINING FRAMEWORK GALLIUM

[75] Inventor: Cynthia T-W. Chu, Princeton Junction, N.J.

[73] Assignee: Mobil Oil Corporation, New York, N.Y.

[21] Appl. No.: 229,052

[22] Filed: Aug. 5, 1988

Related U.S. Application Data

[63] Continuation-in-part of Ser. No. 882,875, Jul. 7, 1986, abandoned, and a continuation-in-part of Ser. No. 882,863, Jul. 7, 1986, abandoned.

[51] Int. Cl.$^4$ .......................... C07C 12/02; C07C 2/52
[52] U.S. Cl. .................................... 585/415; 585/417; 585/418
[58] Field of Search .................. 585/415, 417, 418

[56] References Cited

U.S. PATENT DOCUMENTS

| | | | |
|---|---|---|---|
| 3,926,781 | 12/1975 | Gale | 208/117 |
| 3,970,544 | 7/1976 | Rosinski | 208/111 |
| 4,056,575 | 11/1977 | Gregory et al. | 260/673.5 |
| 4,120,910 | 10/1978 | Chu | 260/673 |
| 4,134,823 | 1/1979 | Bertolacini et al. | 208/65 |
| 4,157,356 | 6/1979 | Bulford et al. | 585/415 |
| 4,180,689 | 12/1979 | Davies et al. | 585/407 |
| 4,304,686 | 12/1981 | Telford | 252/455 Z |
| 4,347,394 | 8/1982 | Detz et al. | 585/419 |
| 4,350,835 | 9/1982 | Chester et al. | 585/415 |
| 4,392,989 | 7/1983 | Chu et al. | 252/455 Z |
| 4,490,569 | 12/1984 | Chu et al. | 585/415 |
| 4,720,602 | 1/1988 | Chu | 585/407 |
| 4,808,295 | 2/1989 | Mavrodin | 208/65 |
| 4,822,939 | 4/1989 | Chu | 585/408 |

FOREIGN PATENT DOCUMENTS 0050021 4/1982 European Pat. Off. .
0107876 11/1982 European Pat. Off. .
0150105 7/1985 European Pat. Off. .
WO84/03879 10/1984 PCT Int'l Appl. .

*Primary Examiner*—Curtis R. Davis
*Attorney, Agent, or Firm*—Alexander J. McKillop; Charles J. Speciale; Marina V. Schneller

[57] ABSTRACT

A catalytic process is provided for converting $C_2$ to $C_{12}$ aliphatic hydrocarbons to aromatics by contacting them under conversion conditions with a crystalline zeolite catalyst having a Constraint Index of about 1 to 12 and containing gallium. Preferably, the zeolite is a low acidity zeolite. In certain embodiments, gallium is inserted into the zeolite framework. Gallium can also be deposited, exchanged or impregnated into the zeolite.

29 Claims, No Drawings

AROMATIZATION OF ALIPHATICS OVER A ZEOLITE CONTAINING FRAMEWORK GALLIUM

CROSS-REFERENCE TO RELATED CASES

This is a continuation in part of two U.S. patent applications, Ser. No. 882,875 and Ser. No. 882,863, each filed on July 7, 1986, both abandoned, each of which is relied upon and incorporated by reference herein.

FIELD OF THE INVENTION

This invention relates to a process for the conversion of a gaseous feed containing a major proportion of $C_2$ to $C_{12}$ aliphatic hydrocarbons to aromatics in the presence of a crystalline zeolite catalyst containing gallium in its crystal framework.

This invention also relates to a process for the conversion of a gaseous paraffinic feed containing a major proportion of $C_3$ to $C_{12}$ aliphatic hydrocarbons to aromatics in the presence of a crystalline low acidity zeolite catalyst containing gallium.

BACKGROUND OF THE INVENTION

Zeolites and alumina have been used in the past in the preparation of catalysts for the production of aromatic hydrocarbons from aliphatic hydrocarbons. The aliphatic hydrocarbon is passed over the catalyst at an elevated temperature in the liquid or vapor phase. Zeolites of various types have been suggested for the preparation of such catalysts. Examples of such zeolities are mordenite and the ZSM varieties, some of which contain gallium as ions which have been impregnated on the zeolite substrate or for which the original cations have been exchanged. However, it has sometimes been considered desirable to improve the yields of aromatic hydrocarbons when using such catalysts.

U.S. Pat. No. 4,180,689 teaches that by using catalysts which contain gallium and which are prepared from specific types of aluminosilicates, improved yields of aromatic hydrocarbons may be obtained if the gallium-containing catalysts are prepared from specific types of aluminosilicates. This patent further discloses that if the gallium is either exchanged for one of the cations or protons or impregnated into the zeolitic cavities, surprisingly high catalytic activity and selectivity are obtained, especially in hydrocarbon conversion process. The feed for this process is a $C_2$-$C_{12}$ feedstock of either a single component or mixtures of saturated and unsaturated hydrocarbons.

U.S. Pat. No. 4,120,910 discloses that aromatic compounds can be produced by contacting, in the absence of added air or oxygen under suitable conversion conditions, a gaseous, paraffinic feed stock containing a high percentage of ethane with a ZSM-5 type crystalline aluminosilicate zeolite catalyst having incorporated therein a minor amount of a metal or metal oxide from Group VIII, IIB, or IB of the Periodic Table. Especially preferred is a zinc-copper mixture.

U.S. Pat. No. 4,304,686 teaches the aromatization of aliphatic hydrocarbons utilizing as catalyst a zeolite having an alumina-silica ratio of 10:1 to 500:1 in which at least some of the cations have been exchanged for gallium ions.

U.S. Pat. No. 4,350,835 teaches a catalytic process for converting a feedstock comprising a high percentage of ethane to aromatics employing as a catalyst a zeolite with a silica-alumina ratio of at least 12 and having incorporated therein a minor amount of gallium.

European Patent Specification Publication No. 50,021 teaches a process for producing aromatic hydrocarbons by contacting a feedstock containing at least 70% by weight of $C_2$ hydrocarbons with a catalyst comprising an aluminosilicate with a silica-alumina molar ratio of at least 5:1 and in which either gallium is deposited thereon, or cations have been exchange with gallium ions.

SUMMARY OF THE INVENTION

One aspect of the invention relates to a process for producing aromatic compounds including contacting under suitable conversion conditions a feed containing a major proportion of $C_2$-$C_{12}$ aliphatic hydrocarbons with an acidic crystalline gallosilicate zeolite catalyst having some portion of zeolitic gallium in tetrahedral coordination therein.

Another aspect of this invention relates to a process for producing aromatic compounds including contacting under suitable conversion conditions a feed containing a major proportion of $C_3$-$C_{12}$ aliphatic hydrocarbons with a ZSM type crystalline aluminosilicate zeolite catalyst having a silica-alumina ratio of at least 550 and an added metal comprising a major proportion of gallium whereby a portion of the aliphatic compounds present in said feed is converted to aromatic compounds.

DESCRIPTION OF SPECIFIC EMBODIMENTS

In certain embodiments the present invention is a process for producing aromatic hydrocarbons comprising bringing into contact at an elevated temperature a hydrocarbon feedstock containing a major proportion of $C_2$-$C_{12}$ aliphatic hydrocarbons with a catalyst comprising a zeolite containing zeolitic gallium in tetrahedral coordination therein. Preferably, the zeolite contains about 0.5 to 5% of zeolitic gallium in its crystal framework based on the weight of the zeolite. Where zeolite contains 0.5 to 5% of zeolitic gallium, it can contain 1 to 10 wt % of total gallium.

Another aspect of the invention relates to a process for producing aromatic compounds including contacting a feed of $C_2$-$C_{12}$ hydrocarbons, under suitable conversion conditions, with a low acidity crystalline gallosilicate zeolite having some portion of zeolitic gallium in tetrahedral coordination therein, as a catalyst.

Another aspect of the invention relates to a process for producing aromatic compounds including contacting a feed of $C_2$-$C_{12}$ hydrocarbons, under suitable conversion conditions, with an acidic crystalline of low acidity gallosilicate having some portion of zeolitic gallium in tetrahedral coordination therein.

In most cases, the catalyst is a crystalline gallosilicate zeolite combined with alumina in the form of extrudate or binder-free pellets. While the dominant framework metal is generally gallium, it is understood that minor amounts of other tetrahedrally coordinated metals may be incorporated in the zeolite structure such as aluminum, boron and titanium. Additional metals may optionally include chromium, vanadium and cobalt species.

The zeolite containing zeolitic gallium in its crystal framework may be prepared using various techniques known in the art, e.g. cocrystallization and vapor insertion wherein a preformed zeolite is subjected to the action of a volatilized gallium compound, e.g. gallium chloride or gallium fluoride, at high temperatures. Preferably, however, the gallium is "inserted" in the liquid phase under alkaline conditions into the crystal framework of a preformed zeolite which is substantially free of gallium. In carrying out the insertion of the gallium-comprising metal by this method, the preformed zeolite may be refluxed in a solution of alkaline material and gallium-comprising metal reagent, e.g. any of various water-soluble compounds such as sulfates and nitrates, ammonia-exchanged to remove or reduce alkali metal cations, and calcined to obtain the catalyst in acid- or hydrogen base form. Any alkaline material can be used for the gallium insertion which is compatible with the gallium-comprising metal reagent, e.g. an aqueous solution of alkali metal hydroxide or carbonate solution such as sodium hydroxide or sodium carbonate with a concentration in the range, for example of about 0.1 to 1N. The refluxing may be carried out at a temperature, for example, of 50° to 100° C. for a period, for example, of about 0.5 to 20 hours. The ammonia-exchange and calcination are carried out under conditions well-known in the art.

Where the catalyst composition is prepared by using a compound of gallium-comprising metal which ionizes in aqueous solution, for example gallium sulfate, some of the gallium ions are generally exchanged with the cations in the zeolite despite the fact that the preparation was directed to insertion into the zeolite. In view of this, the total amount of gallium, i.e. including the zeolitic framework gallium and that ion-exchanged or impregnated on the surfaces of the zeolite crystals, is obviously larger than the amount of zeolitic gallium and is preferably in the range of about 1 to 10 wt.% based on the weight of the catalyst.

Following ammonium ion exchange and calcination, the hydrogen form of the catalyst is obtained. The structure is confirmed by x-ray diffraction, temperature-programmed ammonia sorption, infra-red spectroscopic studies and $^{71}$Ga NMR. $^{71}$Ga NMR indicates the presence of tetrahedral Ga in the zeolite lattic structure as framework atoms. A characteristic IR band at 3620 cm$^{-1}$ is assigned to acidic OH groups associated with framework Ga. The Bronsted acid activity is found to be weaker than analogous aluminum ZSM-5 zeolites. The catalysts of this invention may contain other metals in addition to the gallium, either as part of the crystal framework of the zeolite or deposited on the surface of the zeolite by conventional ion-exchange or impregnation techniques. Thus, one or more suitable metals in Groups I through VIII of the Periodic Table may be added to the gallium-containing catalyst including by way of example zinc, platinum, rhenium, cobalt, titanium, tellurium, sodium, nickel, boron chromium, vanadium, copper, palladium, calcium and rare earth metals.

The gallium-containing catalyst is generally prepared from a zeolite having a Constraint Index (CI) as hereinafter defined of approximately 1 to 12 and in most cases will itself have a CI within the latter range. Moreover, the preformed zeolite and the final catalyst will usually have a silica/alumina ratio of at least about 12. Preferably the silica/alumina ratio is about 500 to 26,000.

The foregoing zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conductive to long times on steam between regenerations by burning carbonaceous deposits with oxygen-containing gas such as air.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 12 are useful, it is preferred in some instances to use zeolites having substantially higher silica/alumina ratios, e.g. 500 or 550 or at least 880 and above. Such "high-silica" or "highly siliceous" zeolites are intended to be included within this description. The high silica to alumina zeolites may be prepared as-synthesized, or by decreasing the aluminum content of low silica to alumina ratio zeolites by steaming, dealuminizing or framework exchange procedures.

In other embodiments the present invention includes a process for producing aromatic hydrocarbons comprising bringing into contact at an elevated temperature a hydrocarbon feedstock containing a major proportion of C3–C12 aliphatic hydrocarbons with a catalyst composition comprising a zeolite having a silica-alumina ratio of at least 550 and an added metal comprising a major proportion of gallium deposited thereon and/or whose cations have been exchanged with ions of said metal. Preferably, all of the added metal is gallium.

The metal comprising gallium in the catalyst composition may be present as ions if cations in the aluminosilicate support have been exchanged with ions of the gallium-containing metal. In the case where the cations in the zeolite have been exchanged for such metal ions, the ions are suitably provided as an aqueous solution of gallium-containing metal salts such as for instance metal sulfate, nitrate or chloride. Such catalysts may be produced by conventional ion exchange techniques and the catalysts so produced are subsequently dried. For example, an aqueous solution of a compound of a metal comprising gallium such as a metal sulfate may be placed in contact with the zeolite at ambient or elevated temperature, e.g. by refluxing. The exchanged zeolite is then separated by decantation followed by filtration, washed several times with deionized water and finally dried. Before addition to the aqueous solution of the gallium compound, the zeolite may be acid treated.

The process of the present invention may be carried out using catalysts in which gallium-comprising metal is impregnated on the surface of the zeolite or is ion-exchanged with cations of the zeolite. However, in accordance with another aspect of the invention, the gallium-comprising metal is preferably incorporated under alkaline conditions into the framework of the zeolite. Any alkaline material can be used for this purpose which is compatible with the gallium-comprising metal reagent, e.g. an aqueous solution of alkali metal hydroxides such as sodium hydroxide with a concentration in the range, for example of about 0.1 to 1N. In carrying out the insertion of the gallium-comprising metal by this method, the zeolite may be refluxed in a solution of alkaline material and gallium-comprising metal reagent, e.g. any of various water-soluble compounds such as sulfates and nitrates, ammonia-exchanged to remove or reduce alkali metal cations, and calcined to obtain the final catalyst.

Where the catalyst composition is prepared by using a compound of gallium-comprising metal which ionizes in aqueous solution, for example gallium nitrate, some of the gallium ions are generally exchanged with the cations in the zeolite even if the preparation was directed to impregnation of or insertion into the zeolite. That portion of the gallium contained but not inserted into the zeolite will exhibit dehydrogenation activity, rather than the Bronsted acidity of gallium inserted into the zeolite framework.

Whichever method of catalyst preparation is used, the amount of gallium present in the catalyst compositions, (metal plus zeolite), may vary for instance between 0.1 and 15, preferably between 0.5 and 10, percent by weight. Of the total amount of added metal, gallium may comprise an amount from over 50 to 100 wt.%. The portion of the added metal which is not gallium may be any of various suitable metals in Groups I through VIII of the Periodic Table including by way of example zinc, platinum, rhenium, cobalt, titanium, tellurium, sodium, nickel, chromium, aluminum, copper, palladium, calcium and rare earth metals.

Although the zeolites utilized in the process have extremely low alumina contents, i.e. silica to alumina mole ratios exceeding 550, they are nevertheless very active. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

The members of the class of zeolites useful herein have an effective pore size of generally from about 5 to about 8 angstroms, such as to freely sorb normal hexane. In addition, the structure must provide constrained access to larger molecules. It is sometimes possible to judge from a known cystal structure whether such constrained access exists. For example, if the only pore windows in a crystal are formed by 8-membered rings of silicon and aluminum atoms, then access by molecules of larger cross-section than normal hexane is excluded and the zeolites is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present invention to entirely judge the usefulness of the particular zeolite solely from theoretical structural considerations.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 angstroms. On the other hand, zeolites which provide relatively free access to the internal zeolite structure have a low value for the Constraint Index, and usually pores of large size, e.g. greater than 8 angstroms. The method by which Constraint Index is determined is described fully in U.S. Pat. No. 4,016,218, incorporated herein by reference for details of the method.

Constraint Index (CI) values for some typical materials are:

|  | CI (at test temperatures) | |
| --- | --- | --- |
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |
| ZSM-38 | 2 | (510° C.) |
| ZSM-48 | 3.5 | (538° C.) |
| ZSM-50 | 2.1 | (427° C.) |
| TMA Offretite | 3.7 | (316° C.) |
| TEA Mordenite | 0.4 | (316° C.) |
| Clinoptilolite | 3.4 | (510° C.) |
| Mordenite | 0.5 | (316° C.) |
| REY | 0.4 | (316° C.) |
| Amorphous Silica-alumina | 0.6 | (558° C.) |
| Dealuminized Y | 0.5 | (510° C.) |
| Erionite | 38 | (316° C.) |
| Zeolite Beta | 0.6–2.0 | (316° C.–399° C.) |

The above-described Constraint Index is an important and even critical definition of these zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of interest herein within the approximate range of 1 to 12.

The class of zeolites defined herein is exemplified by ZSM-5, ZSM-11, ZSM-12, ZSM-23, ZSM-35, ZSM-38, ZSM-48, and other similar materials. The compositions, methods of preparation, and X-ray diffraction patterns of these zeolites are typified in the following patents: ZSM-5 in U.S. Pat. No. 3,702,886 and Re. No. 29,948; ZSM-11 in U.S. Pat. No. 3,709,979; ZSM-12 in U.S. Pat. No. 3,832,449; ZSM-23 in U.S. Pat. No. 4,076,842; ZSM-35 in U.S. Pat. No. 4,016,245; ZSM-38 in U.S. Pat. No. 4,046,859 and ZSM-48 in U.S. Pat. No. 4,350,835. The entire disclosures of these patents are incorporated by reference insofar as their disclosures are necessary to identify the respective zeolites.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is in most cases at least 12 and may be as high as about 26,000. The incorporation of the identified patents should therefore not be construed as limiting the disclosed crystalline zeolites to those having the specific silica-alumina mole ratios discussed therein, it now being known that such zeolites may have much higher silica-alumina ratios and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at about 540° C. for one hour, for example, followed by base exchange with ammonium salts followed by calcination at about 540° C. in air. The presence of organic cations in the forming solution may not be absolutely essential to the formation of this type zeolite; however, the presence of these cations does appear to favor the formation of this special class of zeolite. In many cases, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 500 and up to about 26,000, and a dried crystal density of not less than about 1.6 grams per cubic centimeter. The dry density for known structures may be calculated from the number of silicon plus aluminum atoms per 1000 cubic angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used.

Thus, the original alkali metal of the zeolite may be replaced by ion exchange with gallium and, if desired other suitable metal cations, of Groups I through VIII of the Periodic Table as mentioned previously.

In practicing a particularly desired chemical conversion process, it may be useful to incorporate the above-described crystalline zeolite with a matrix comprising another material resistant to the temperature and other conditions employed in the process. Such matrix material is useful as a binder and imparts greated resistance to the catalyst for the severe temperature, pressure and reactant feed stream velocity conditions encountered in many conversion processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, kickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as silica, alumina, silica-alimina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The feed stream to the process of this invention contains at least 50% by weight of at least one aliphatic hydrocarbon containing 2 to 12 carbon atoms. The hydrocarbon may be straight chain, open chain or cyclic and may be saturated or unsaturated. Some contemplated hydrocarbons are ethane, propane, propylene, n-butane, n-butenes, isobutane, isobutene, straight- and branch chain hexanes, hexenes, octanes, octenes, decanes and decenes, cyclohexane and cyclohexene.

The process of this invention is conducted so that a feed containing a high percentage, i.e. at least 50 wt.% of $C_2$-$C_{12}$ aliphatic hydrocarbons is contacted with a suitable zeolite catalyst in a reaction zone, such as, for example, a fixed bed of catalyst composition under effective conversion conditions. In a typical embodiment of the process of this invention, the feed stream is introduced into the reaction zone at a temperature within the range of 900° F. and about 1400° F., a pressure within the range of atmospheric pressure to 400 psig and a LHSV of 0.1 to 5.

Preferred temperatures for the process of this invention fall within the range of about 900° F. to about 1250° F. and preferred pressures fall within the range of one atmosphere to 100 psig. A preferred LHSV is between 0.3 and 3.

The effluent from the reaction zone is separated and distilled to remove the desired aromatic product and the remainder is recycled for further reaction.

The following examples further illustrate the invention.

EXAMPLE 1

This example illustrates the preparation and use of a gallium-containing zeolite catalyst under the invention in which at least some gallium is inserted into the crystal framework, of the zeolite under alkaline conditions.

Ten grams of a hydrogen or acid-base ZSM-5 zeolite having a silica-alumina ratio of 880 were refluxed with 2.5 grams of $Ga_2(SO_4)_3.18H_2O$ in a solution of 0.2N NaOH for two hours. The catalyst was then ammonia-exchanged and calcined at 538° C. in air for 4 hours. The final catalyst contained 4.0 wt% of added gallium of which 29% was determined by the ammonia TPD method to be incorporated within the framework of the zeolite crystals.

This catalyst was tested for aromatization activity by loading it into a reactor and introducing n-hexane at a temperature of 538° C. (1000° F.), atmospheric pressure, and an LHSV of 0.59. After various times on stream, the product was analyzed. Hydrogen and light gases ($C_1$-$C_3$) were analyzed by a refiney gas analysis GC, $C_3+$ gases were analyzed on a n-octane-porasil C column, and liquid products were analyzed on a DB-1 Durabond capillary column. The results are shown in Table 1 where the numbers all signify weight percent of product except as indicated, "$C_1+C_2$" is the total of methane and ethane, "$C_2=+$" is the total of ethylene and higher aliphatics and "Aromatics Selectivity" is defined as follows.

$$\frac{\text{Aromatics yield (wt. \%)}}{C_1 + C_2\text{(wt. \%)} + \text{aromatics yield (wt. \%)}}$$

EXAMPLE 2

The procedure of Example 1 was followed except that the catalyst preparation solution contained 15 grams of the ZSM-5 which was refluxed with 3.75 grams of $Ga_2(SO_4)_3.18H_2O$ and finished catalyst contained 7.3 wt.% of added gallium, 65% of which was in the framework of the zeolite crystals. The results are shown in Table 1.

Use of a zeolite catalyst containing zeolitic gallium in tetrahedral coordination therein in an aromatization process in many cases yields a product in which the ratio of aromatics to the total of methane and ethane ($C_1+C_2$) is higher than that obtained under equivalent conditions except that all the gallium is ion-exchanged or impregnated at the surface of the zeolite rather than part being in the crystal framework. This is significant since methane does not usually yield may aromatics or aromatics percursors on recycling, while ethane is more difficult to aromatize than higher alkanes.

EXAMPLE 3

This example illustrates the preparation and use of a catalyst under the invention in which gallium is deposited in a zeolite substrate by ion exchange.

15 grams of $Ga(NO_3)_3xH_2O$ were dissolved in $H_2O$ and impregnated on 7.5 grams of a ZSM-5 zeolite with the same silica-alumina ratio as Examples 1 and 2, viz. 850. The catalyst was then calcined in air at 538° C. The finished catalyst contained 10.2 wt.% of deposited gallium. The catalyst was then tested for aromatization activity as described in Example 1. The results are shown in Table 1.

6.8 wt.% of deposited gallium. The results of aromatization of n-hexane with this catalyst are shown in Table 2.

COMPARATIVE EXAMPLE B

TABLE 1

| Example | 1 | | | 2 | | | 3 | |
|---|---|---|---|---|---|---|---|---|
| Time on Stream(hrs.) | 7 | 12 | 18 | 6 | 12 | 17 | 7 | 30 |
| $H_2$ | 1.19 | 2.87 | 1.91 | 3.08 | 2.35 | 2.31 | 1.86 | 0.96 |
| Methane | 2.74 | 3.82 | 5.85 | 3.82 | 4.41 | 4.92 | 0.01 | 0.74 |
| Ethane | 4.62 | 8.24 | 6.07 | 9.70 | 7.50 | 7.48 | 4.82 | 1.56 |
| Propane | 9.41 | 9.56 | 13.24 | 10.04 | 10.82 | 13.76 | 2.50 | 1.75 |
| n-Butane | 3.64 | 3.08 | 3.92 | 2.32 | 2.80 | 3.44 | 0.74 | 0.88 |
| i-Butane | 5.21 | 5.34 | 5.65 | 3.08 | 3.60 | 5.85 | 1.70 | 2.60 |
| n-Pentane | 0.04 | 0.02 | 0.06 | 0.04 | 0.05 | 0.02 | 0.08 | 0.08 |
| i-Pentane | 1.98 | 0.72 | 0.10 | 0.04 | 0.15 | 0.03 | 0.73 | 0.95 |
| n-Hexane | 15.57 | 15.02 | 12.85 | 4.62 | 8.00 | 10.17 | 56.83 | 70.73 |
| $C_6+$ Aliphatics | 3.64 | 0.72 | 0.73 | 6.09 | 4.46 | 0.10 | 0.80 | 1.07 |
| Ethylene | 2.82 | 6.26 | 4.12 | 3.53 | 2.88 | 3.58 | 3.79 | 2.31 |
| Propylene | 9.70 | 10.81 | 12.05 | 5.84 | 7.34 | 10.82 | 5.72 | 3.74 |
| $C_4$ Olefins | 5.10 | 5.35 | 2.21 | 0.24 | 1.19 | 1.82 | 4.11 | 4.72 |
| $C_5$ Olefins | 2.77 | 0.62 | 0.39 | 2.14 | 0.36 | 0.15 | 0.55 | 0.61 |
| Benzene | 14.56 | 11.44 | 13.30 | 17.32 | 17.68 | 12.78 | 4.32 | 2.89 |
| Toluene | 9.08 | 7.47 | 8.60 | 13.15 | 12.03 | 7.97 | 3.69 | 1.79 |
| $C_8$ Aromatics | 5.30 | 6.67 | 6.41 | 10.09 | 9.59 | 8.50 | 4.45 | 1.81 |
| $C_9$ Aromatics | 1.39 | 1.77 | 2.03 | 2.19 | 2.44 | 2.41 | 1.61 | 0.86 |
| $C_{10}$ Aromatics | 0.90 | 0.25 | 0.50 | 1.50 | 1.35 | 1.22 | 0.41 | 0.21 |
| $C_{11}$ Aromatics | 0.35 | — | 0.03 | 1.17 | 1.12 | 0.91 | 0.24 | 0.07 |
| Material Balance (% recovered) | | | | | | | | |
| C | 106 | 95 | 103 | 100 | 100 | 100 | 95 | 98 |
| H | 97 | 99 | 102 | 99 | 96 | 99 | 98 | 101 |
| $C_1 + C_2$ | 7.45 | 12.41 | 12.15 | 13.95 | 12.20 | 12.70 | 5.94 | 2.33 |
| Aromatics | 31.96 | 28.42 | 31.47 | 46.86 | 45.27 | 36.39 | 15.00 | 7.72 |
| $C_2 = +$ Aromatics | 60.59 | 59.17 | 56.38 | 39.19 | 42.53 | 50.91 | 79.06 | 89.95 |
| Selectivity | 81.10 | 69.61 | 72.15 | 77.06 | 78.77 | 74.13 | 71.63 | 76.82 |

The aromatization activity of the catalysts of Examples 1, 2 and 3 under this invention as indicated by the results of Table 1 show a relatively high aromatics selectivity and a concomitant low production of C1+C2 which are considered particularly undesirable by-products of aromatics production. Moreover, comparison of the results of Examples 1 and 2 wherein the catalyst contained a substantial proportion of gallium inserted into the framework of the gallium under alkaline conditions, with those of Example 3 wherein the gallium was deposited on the zeolite by ion exchange, shows that higher aromatics selectivities are obtained after a time on stream of 7 hours or less with catalysts containing some inserted gallium than those containing all exchanged gallium.

COMPARATIVE EXAMPLE A

This example illustrates the preparation and use of a catalyst utilizing a zeolite in which the silica-alumina ratio is lower than that defined by this invention.

The procedure of Example 3 was followed except that the silica-alumina ratio of the hydrogen-base ZSM-5 zeolite was 70. The finished catalyst contained This example illustrates the preparation and use of a catalyst in which the silica-alumina ratio is lower than that defined by the invention and which contains gallium deposited by impregnation.

2 grams of $Ga(NO_3)_3 \times H_2O$ were dissolved in 10 cc of water and 5 grams of a hydrogen base ZSM-5 zeolite with a silica-alumina ratio of 40 were added to the solution. The mixture was dried overnight and calcined at 538° C. for 6 hours. The finished catalyst contained 7.3 wt.% of impregnated gallium. Use of this catalyst for aromatization of n-hexane as described in Example 1 yielded the results shown in Table 2.

COMPARATIVE EXAMPLE C

This example illustrates the use of a catalyst consisting of a zeolite having a lower silica-alumina ratio than is defined by the invention and no added metal.

n-Hexane was subjected to aromatization using the conditions of Example 1 and a catalyst consisting of a hydrogen base ZSM-5 zeolite with a silica-alumina ratio of 70 and no added metal such as gallium. The results obtained are shown in Table 2.

TABLE 2

| Example | A | | | | | B | | | C |
|---|---|---|---|---|---|---|---|---|---|
| Time on Stream | 7.5 | 14.5 | 21.5 | 43.5 | 60 | 7.5 | 15 | 31.5 | 5.5 |
| $H_2$ | 4.68 | 4.05 | 3.70 | 3.90 | 3.62 | 4.29 | 3.68 | 3.69 | 0.23 |
| Methane | 6.31 | 5.22 | 4.89 | 4.84 | 4.73 | 8.94 | 7.67 | 5.52 | 8.15 |
| Ethane | 21.44 | 18.10 | 15.46 | 16.91 | 16.52 | 22.88 | 19.63 | 21.36 | 14.99 |
| Propane | 18.71 | 17.18 | 15.45 | 15.33 | 15.14 | 8.21 | 12.31 | 13.79 | 36.94 |
| n-Butane | 2.11 | 3.01 | 3.25 | 3.20 | 3.01 | 0.21 | 0.43 | 1.97 | 1.54 |
| i-Butane | 1.04 | 2.25 | 3.00 | 3.60 | 3.08 | 0.18 | 0.25 | 1.11 | 1.80 |
| n-Pentane | 0.02 | 0.01 | 0.02 | 0.04 | 0.02 | 0.00 | 0.00 | 0.04 | 0.05 |
| i-Pentane | 0.01 | 0.18 | 0.42 | 0.45 | 0.29 | 0.03 | 0.05 | 0.26 | 0.10 |

TABLE 2-continued

| Example | A | | | | | B | | | C |
|---|---|---|---|---|---|---|---|---|---|
| Time on Stream | 7.5 | 14.5 | 21.5 | 43.5 | 60 | 7.5 | 15 | 31.5 | 5.5 |
| n-Hexane | 0.56 | 0.62 | 1.82 | 2.37 | 5.04 | 0.06 | 0.06 | 0.16 | 0.23 |
| $C_6$ + Aliphatics | 0.00 | 0.07 | 0.04 | 0.04 | 0.13 | 0.00 | 0.04 | 0.01 | 2.66 |
| Ethylene | 1.75 | 2.98 | 3.80 | 4.56 | 3.86 | 0.64 | 0.55 | 1.99 | 2.76 |
| Propylene | 2.28 | 3.89 | 5.34 | 6.20 | 5.25 | 0.72 | 1.09 | 2.46 | 3.04 |
| $C_4$ Olefins | 0.92 | 1.81 | 2.68 | 3.13 | 2.92 | 0.07 | 0.19 | 0.89 | 1.07 |
| $C_5$ Olefins | 0.01 | 0.03 | 0.14 | 0.18 | 0.21 | 0.01 | 0.04 | 0.04 | 0.85 |
| Benzene | 13.03 | 14.11 | 12.06 | 10.92 | 11.39 | 15.97 | 16.35 | 13.16 | 4.14 |
| Toluene | 13.63 | 13.31 | 12.74 | 10.80 | 10.05 | 19.91 | 19.07 | 15.81 | 8.67 |
| $C_8$ Aromatics | 8.68 | 8.79 | 9.79 | 8.54 | 9.10 | 9.48 | 10.83 | 10.77 | 6.06 |
| $C_9$ Aromatics | 1.44 | 1.59 | 2.78 | 2.56 | 3.44 | 1.33 | 1.66 | 2.02 | 1.43 |
| $C_{10}$ Aromatics | 2.17 | 1.62 | 1.33 | 1.10 | 1.10 | 3.36 | 2.94 | 2.67 | 1.89 |
| $C_{11}$ Aromatics | 1.21 | 1.17 | 1.31 | 1.33 | 1.11 | 3.70 | 3.16 | 2.28 | 3.41 |
| $C_1 + C_2$ | 29.11 | 24.30 | 21.13 | 22.63 | 22.05 | 33.25 | 28.34 | 27.91 | 23.19 |
| Aromatics | 42.14 | 42.30 | 41.55 | 36.68 | 37.54 | 56.16 | 56.07 | 48.50 | 25.66 |
| $C_2$ =+ Aromatics | 28.75 | 33.40 | 37.32 | 40.69 | 40.41 | 10.59 | 15.59 | 23.59 | 51.15 |
| Selectivity | 59.14 | 63.51 | 66.29 | 61.84 | 63.00 | 62.81 | 66.43 | 63.47 | 52.53 |

Comparison of the results of Examples 1 to 3 under the invention with those of Comparative Examples A to C wherein at least one parameter defined by the invention was not employed, shows that substantially higher aromatics selectives and lower production of C1+C2 were obtained with the examples under the invention than with the comparative examples.

What is claimed is:

1. In a process for producing aromatic compounds from aliphatic hydrocarbons under conditions effective to produce aromatic product, methane and ethane, the improvement which comprises in combination contacting under said conditions, a feed containing at least 50 weight percent of $C_3$ to $C_{12}$ aliphatic hydrocarbons with a catalyst comprising a crystalline zeolite characterized by a Constraint Index within the approximate range of 1 to 12 and a silica to alumina ratio of at least 550 and an added metal comprising at least 50 weight percent of gallium, the weight of added metal in said catalyst being between about 0.5 to about 10 percent based on the total weight of catalyst whereby aliphatic hydrocarbons present in said feed are converted to aromatic compounds; and thereby increasing the selectivity of the process for said aromatic compounds and decreasing its selectivity for methane and ethane production.

2. The process of claim 1 wherein said added metal consists solely of gallium.

3. The process of claim 2 wherein at least 0.5% of said gallium is inserted in to the framework of said zeolite under alkaline conditions.

4. The process of claim 1 wherein the conversion conditions include a temperature of from about 482° C. to about 760° C., a pressure of from about $1 \times 10^5$ to about $28.6 \times 10^5$ pascal and LHSV of from about 0.1 to about 5.

5. The process of claim 1 wherein said crystalline zeolite is selected from the group consisting of ZSM-5, ZSM-11, ZSM-12, ZSM-35, ZSM-38 and ZSM-48.

6. The process of claim 1 wherein said zeolite is ZSM-5.

7. The process of claim 1 wherein said zeolite is ZSM-11.

8. The process of claim 1 wherein said zeolite is ZSM-12.

9. The process of claim 1 wherein said zeolite is ZSM-35.

10. The process of claim 1 wherein said zeolite is ZSM-38.

11. The process of claim 1 wherein said zeolite is ZSM-48.

12. The process of claim 2 wherein the concentration of gallium in said catalyst is between about 0.5 and about 10 percent by weight.

13. The process of claim 2 wherein the weight of gallium in said catalyst is between about 0.5 and about 10 percent, said zeolite is ZSM-5, said catalyst is composited with a porous matrix material in a proportion of between about 5 and about 80 percent by weight of catalyst composition in the dry composite, and conversion conditions include a temperature of from about 593.3° C. to about 676.7° C., a pressure of from about $1 \times 10^5$ to about $7.9 \times 10^5$ pascal and a LHSV of about 0.3 to about 3.

14. In a process for producing aromatic compounds from aliphatic hydrocarbons under conditions effective to produce aromatic product, methane and ethane, the improvement which comprises in combination contacting under said conditions, a feed containing at least 50 weight percent of $C_3$ to $C_{12}$ aliphatic hydrocarbons with a catalyst comprising a crystalline zeolite characterized by a Constraint Index within the approximate range of 1 to 12 and a silica to alumina ratio of at least 550 and gallium, the weight of added gallium in said catalyst being between about 0.5 to about 10 percent based on the total weight of catalyst wherein at least 0.5% of said gallium is inserted into the framework of said zeolite under alkaline conditions, whereby aliphatic hydrocarbons present in said feed are converted to aromatic compounds; and thereby increasing the selectivity of the process for said aromatic compounds and decreasing its selectivity for methane and ethane production.

15. The process of claim 14 wherein the conversion conditions include a temperature of from about 482° C. to about 760° C., a pressure of from about $1 \times 10^5$ to about $28.6 \times 10^5$ pascal and a LHSV of from about 0.1 to about 5.

16. The process of claim 14 wherein said crystalline zeolite is selected from the group consisting of ZSM-5, ZSM-11, ZSM-12, ZSM-35, ZSM-38 and ZSM-48.

17. The process of claim 14 wherein said zeolite is ZSM-5.

18. The process of claim 14 wherein said zeolite is ZSM-11.

19. A process for producing aromatic compounds which comprises contacting under conversion conditions effective to convert aliphatic hydrocarbons to said aromatic compounds, a feed containing at least 50 weight percent of $C_2$ to $C_{12}$ aliphatic hydrocarbons with a catalyst comprising a crystalline zeolite characterized by a Constraint Index within the approximate range of 1 to 12 and containing 1 to 10 wt. % gallium, wherein the catalyst contains about 0.5 to 5 wt.% of said zeolitic gallium, wherein the catalyst is prepared by inserting said gallium into the crystal framework of a preformed zeolite in the liquid phase under alkaline conditions, whereby aliphatic hydrocarbons present in said feed are converted to aromatic compounds, and recovering said aromatic compounds.

20. The process of claim 19 in which the silica/alumina ratio of said zeolite is at least about 12.

21. The process of claim 19 in which the silica/alumina ratio of said zeolite is about 500 to 26,000.

22. The process of claim 19 wherein said crystalline zeolite is selected from the group consisting of ZSM-5, ZSM-11, ZSM-12, ZSM-35, ZSM-38 and ZSM-48.

23. The process of claim 22 wherein said zeolite is ZSM-5.

24. The process of claim 22 wherein said zeolite is ZSM-11.

25. The process of claim 22 wherein said zeolite is ZSM-12.

26. The process of claim 22 wherein said zeolite is ZSM-35.

27. The process of claim 22 wherein said zeolite is ZSM-38.

28. The process of claim 22 wherein said zeolite is ZSM-48.

29. The process of claim 1, wherein the silica-alumina ratio of said zeolite is about 500 to 26,000.

* * * * *